US010201506B2

United States Patent
Brown et al.

(10) Patent No.: US 10,201,506 B2
(45) Date of Patent: *Feb. 12, 2019

(54) NANOPARTICULATE AND MACROPARTICULATE FORMULATIONS

(71) Applicant: Cephalon, Inc., Frazer, PA (US)

(72) Inventors: Peter D. Brown, West Chester, PA (US); Anthony S. Drager, Thorndale, PA (US)

(73) Assignee: CEPHALON, INC., North Wales, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,421

(22) Filed: Feb. 6, 2017

(65) Prior Publication Data

US 2017/0143640 A1    May 25, 2017

Related U.S. Application Data

(63) Continuation of application No. 14/772,540, filed as application No. PCT/US2014/023922 on Mar. 12, 2014, now Pat. No. 9,598,377.

(Continued)

(51) Int. Cl.

| | |
|---|---|
| *A61K 9/51* | (2006.01) |
| *A61K 38/02* | (2006.01) |
| *A61K 9/50* | (2006.01) |
| *A61K 31/7088* | (2006.01) |
| *A61K 31/4184* | (2006.01) |
| *A61K 9/14* | (2006.01) |
| *C07D 235/16* | (2006.01) |

(Continued)

(52) U.S. Cl.
CPC ............ *A61K 9/5146* (2013.01); *A61K 9/145* (2013.01); *A61K 9/5031* (2013.01); *A61K 9/5089* (2013.01); *A61K 31/4184* (2013.01); *A61K 31/7088* (2013.01); *A61K 38/02* (2013.01); *A61K 47/60* (2017.08); *A61K 47/6935* (2017.08); *C07D 235/16* (2013.01)

(58) Field of Classification Search
None
See application file for complete search history.

(56) References Cited

U.S. PATENT DOCUMENTS

| | | | |
|---|---|---|---|
| 6,117,454 A | 9/2000 | Kreuter et al. | |
| 7,348,031 B2 * | 3/2008 | Montasser | ............... B01J 13/14 424/400 |

(Continued)

FOREIGN PATENT DOCUMENTS

| | | |
|---|---|---|
| CA | 2097801 A1 | 6/1992 |
| JP | 02-293041 A | 12/1990 |

(Continued)

OTHER PUBLICATIONS

Batyrbekov et al., Polyurethane as Carriers of Antituberculosis Drugs, Chapter 8.

(Continued)

*Primary Examiner* — Aradhana Sasan
(74) *Attorney, Agent, or Firm* — Baker & Hostetler LLP (57) ABSTRACT

The present invention is directed to particles prepared via the polymerization of at least one surfactant and an isocyanate-containing compound. Pharmaceutical compositions prepared using these particles are also described.

22 Claims, 2 Drawing Sheets

Related U.S. Application Data (60) Provisional application No. 61/776,964, filed on Mar. 12, 2013.

(51) Int. Cl.
  *A61K 47/60* (2017.01)
  *A61K 47/69* (2017.01)

(56) References Cited

U.S. PATENT DOCUMENTS

| | | | |
|---|---|---|---|
| 2007/0042182 A1* | 2/2007 | Markus | A01N 65/00 428/402.2 |
| 2007/0092467 A1* | 4/2007 | Rozot | A61K 8/42 424/70.1 |
| 2010/0210701 A1 | 8/2010 | Cephalon | |
| 2010/0323020 A1 | 12/2010 | Gokhale | |
| 2012/0141416 A1* | 6/2012 | Demeule | A61K 47/48246 424/85.7 |
| 2012/0231069 A1* | 9/2012 | Nowotnik | B82Y 5/00 424/450 |

FOREIGN PATENT DOCUMENTS

| | | |
|---|---|---|
| WO | 1992/010287 | 6/1992 |
| WO | WO 2002/0209862 | 2/2002 |
| WO | 2004/008101 A2 | 1/2004 |
| WO | 2007/102888 A2 | 9/2007 |
| WO | 2009/037310 A2 | 3/2009 |
| WO | WO 2010/063493 | 6/2010 |
| WO | 2010/083276 A1 | 7/2010 |
| WO | WO 2014/075035 | 5/2014 |

OTHER PUBLICATIONS

Bowen P., "Particle Size Distribution Measurement from Millimeters to Nanometers and from Rods to Platelets" Journal of Dispersion Science and technology, Taylor & Francis Group, New York, NY, vol. 23, No. 5, pp. 631-662, Jan. 1, 2002.

Gao et al., pH-Responsive Nanoparticles for Drug Delivery, Molecular Pharmaceutics, Sep. 2010.

Gaudin et al., Core-Shell Biocompatible Polyurethane Nanocapsules Obtained by Interfacial Step Polymerisation in miniemulsion, Colloids and Surfaces A: Physicochemical and Engineering Aspects, 331, pp. 133-142, 2008.

Kothamasu et al., Nanocapsules: The Weapons for Novel Drug Delivery Systems, BioImpacts, 2(2), 71-81, 2012.

Nagavarma BVN, et al., Different Techniques for Preparation of Polymeric Nanoparticles—A Review, Asian Journal of Pharmaceutical and Clinical Research, vol. 5, Suppl 3, Jun. 2012.

Proposed Synthetic Route to pH Responsive/Derivatizable Cross-Linker, Journal of Organic Chemistry, 52(20), 4531-6, 1987.

Rao et al., Polymer nanoparticles: Preparation techniques and size-control parameters, Progress in Polymer Science, 36, pp. 887-913, 2011.

Vauthier et al., Methods for the Preparation and Manufacture of Polymeric Nanoparticles, Pharmaceutical Research, vol. 26, No. 5, May 2009.

Welsh et al., "Chitosan Cross-Linking with a Water-Soluble, Blocked Diisocyanate. 1 . Solid State", Biomacromolecules, vol. 3, pp. 1370-1374, Sep. 2002.

Subedi R K et al: "Preparation and characterization of solid lipid nanoparticles loaded with doxorubicin", European Journal of Pharmaceutical Sciences, Elsevier, Amsterdam, NL, vol. 37, No. 3-4, Jun. 28, 2009, pp. 508-513.

Dongmei Ren et al: "Protein Nanocapsules Containing Doxorubicin as a pH-Responsive Delivery System", Small, vol. 7, No. 8, Apr. 18, 2011, pp. 1051-1060.

Anning Wang et al: "Temperature- and pH-responsive nanoparticles of biocompatible polyurethanes for doxorubicin delivery", International Journal of Pharmaceutics, vol. 441, No. 1-2, Jan. 1, 2013, pp. 30-39.

* cited by examiner

NANOPARTICULATE AND MACROPARTICULATE FORMULATIONS

CROSS REFERENCE TO RELATED APPLICATIONS

This application is a continuation of U.S. application Ser. No. 14/772,540, filed Sep. 3, 2015, which is the National Stage of International Application No. PCT/US2014/023922, filed Mar. 12, 2014, which claims the benefit of U.S. Provisional Application No. 61/776,964, filed Mar. 12, 2013, the entireties of which are incorporated by reference herein.

TECHNICAL FIELD

The present invention is directed to particles prepared via the polymerization of at least one surfactant and an isocyanate-containing compound. Pharmaceutical compositions prepared using these particles are also described.

BACKGROUND

Nanoparticles and macroparticles, including nanocapsules, have been investigated as carriers for drug delivery. Development of new particles that can effectively protect therapeutic agents from premature degradation in order to increase bioavailability are still needed, however.

Bendamustine, 4-{5-[bis(2-chloroethyl)amino]-1-methyl-2-benzimidazolyl} butyric acid has the following formula:

Bendamustine hydrochloride was initially synthesized in 1963 in the German Democratic Republic (GDR) and was available from 1971 to 1992 there under the tradename Cytostasan®. See, e.g., W. Ozegowski and D. Krebs, IMET 3393 γ-[1-methyl-5-bis-β-chloroethyl)-aminobenzimidazolo-(2)]-butyryl chloride, a new cytostatic agent of the group of benzimidazole nitrogen mustards. Zbl. Pharm. 110, (1971) Heft 10, 1013-1019, describing the synthesis of bendamustine hydrochloride monohydrate. Since that time, it has been marketed in Germany under the tradename Ribomustin®. Bendamustine is an alkylating agent that has been shown to have therapeutic utility in treating diseases such as chronic lymphocytic leukemia, Hodgkin's disease, non-Hodgkin's lymphoma, multiple myeloma, and breast cancer. Bendamustine hydrochloride is marketed in the United States under the tradename Treanda®.

While bendamustine has demonstrated efficacy, it is known to be unstable, especially in aqueous solutions, leading to technical difficulties in its preparation and administration. As a result, bendamustine hydrochloride has only been marketed as a lyophilized preparation that is reconstituted immediately prior to infusion. In addition, because of this instability in an aqueous environment, the drug has a relatively short-half life, which limits the suitability of the current formulations for treating certain types of solid tumors. Because of the limitations associated with the currently available formulations, the expansion of the therapeutic use of bendamustine has been limited. New formulations of bendamustine are needed.

SUMMARY

The present invention is directed to methods of preparing bendamustine free base-containing particles comprising forming an emulsion by mixing a continuous phase comprising an organic solvent, a dispersed phase comprising an aqueous solution of a pharmaceutically acceptable salt of bendamustine, and at least one polyhydric alcohol surfactant; treating the emulsion with an amount of base sufficient to convert the pharmaceutically acceptable salt of bendamustine to bendamustine free base; treating the emulsion with a compound comprising at least two isocyanate moieties; allowing sufficient time for the isocyanate-containing compound to polymerize with the at least one polyhydric alcohol surfactant at the water-polyhydric alcohol interface to form the bendamustine free base-containing particles; and optionally isolating the particles.

The invention is also directed to methods of preparing particles comprising forming an emulsion comprising a continuous phase comprising an organic solvent, a dispersed aqueous phase, and at least one polyhydric alcohol surfactant; treating the emulsion with a compound comprising at least two isocyanate moieties; allowing sufficient time for the compound comprising at least two isocyanate moieties to polymerize with the at least one polyhydric alcohol surfactant at the aqueous phase-polyhydric alcohol interface to form the particles; and optionally isolating the particles.

Particles, including nanocapsules, prepared according to these methods are also described, as well as pharmaceutical compositions including the particles of the invention. Methods of using these particles are also described.

DETAILED DESCRIPTION OF ILLUSTRATIVE EMBODIMENTS

The present invention is directed to methods of preparing particles. In preferred methods of the invention, the particles are bendamustine free base-containing particles, preferably, bendamustine free base-containing nanoparticles.

Within the scope of the invention, "particles" can be nanoparticles or macroparticles. "Nanoparticles" are understood in the art to have an average diameter of between about 10 nm and 1000 nm. Preferably, the particles have an average diameter of between about 50 nm and about 300 nm, about 60 nm to about 600 nm, about 20 nm to about 800 nm, or about 20 nm to about 600 nm. "Macroparticles" formed according to the invention are understood in the art to have an average diameter of greater than 0.2 µm and up to 100 µm or up to 1000 µm. Particle size determination for any of the materials of the invention can be achieved using any methods known in the art. Suitable methods for particle size determination include dynamic light scattering (DLS) or transmission electron microscopy (TEM) methods.

Also within the scope of the invention, particles that are "nanoparticles" can be nanocapsules. "Nanocapsules" are generally spherically-shaped with a continuous, polymeric shell and an internal space suitable for encapsulating therapeutic agents. Nanocapsules are understood in the art to have an average diameter of between about 10 nm and 1000 nm. Preferably, the nanocapsules have an average diameter of between about 50 nm and about 300 nm, about 60 nm to about 600 nm, about 20 nm to about 800 nm, or about 20 nm to about 600 nm.

"Therapeutic agents," as used within the present invention, refers to any compound useful for therapeutic or diagnostic purposes. Therapeutic agents that can be used in the present invention include any water-soluble agent, such as, for example, peptides, enzymes, proteins, antibodies, antibody fragments, aptamers, polynucleotides, pharmaceutical compounds, including pharmaceutically acceptable salts of pharmaceutical compounds. A particularly preferred therapeutic agent is bendamustine.

One exemplary embodiment of the invention includes nanocapsules comprising a polymeric shell and a core containing bendamustine free base. Preferably, these nanocapsules have an average diameter of between about 10 nm about 1000 nm. Alternatively, these nanocapsules have an average diameter of between about 60 nm and about 600 nm.

Particles of the invention are prepared by forming an emulsion. "Emulsions" are understood in the art to be a mixture of liquids that are normally immiscible. By manual or mechanically mixing, these normally immiscible liquids form a dispersed phase within a dispersion medium (or "continuous phase"). With oil-in water emulsions, the "oil" is generally the dispersed, "droplet" phase and the water (or an aqueous solution) is the dispersion medium. With water-in-oil emulsions, the aqueous, water-containing phase becomes the dispersed, "droplet" phase within a continuous phase of the "oil" or other water-immiscible solvent used as the dispersion medium. The size of the droplets within the emulsion can be engineered to be larger or smaller depending on factors known in the art, for example, the type of mixing, the mixing speed, the mixing time, properties of the oil, the ratio of oil to water, etc.

Emulsions within the scope of the invention can be either nanoemulsions or macroemulsions. Nanoemulsions have an average droplet diameter for the dispersed phase ranging from about 10 nm to about 1000 nm. Other preferred nanoemulsions have average droplet diameters of between about 50 nm and about 300 nm, about 60 nm to about 600 nm, about 20 nm to about 800 nm, or about 20 nm to about 600 nm. Macroemulsions have a mean droplet diameter greater than about 1μm, up to about 100 μm. Suitable methods for determining the size of the droplets include dynamic light scattering (DLS) or transmission electron microscopy (TEM) methods.

Emulsions of the invention are formed by mixing a continuous phase comprising an organic solvent, a dispersed aqueous phase, and at least one polyhydric alcohol surfactant. The aqueous phase preferably includes water and a water soluble therapeutic agent, such as, for example, a peptide or protein, or a polynucleotide. The therapeutic agent can also be a small molecule drug compound. Pharmaceutically acceptable salts of therapeutic agents can also be used within the scope of the invention.

In preferred embodiments of the invention, the emulsion is formed by mixing a continuous phase comprising an organic solvent, a dispersed phase comprising an aqueous solution of a pharmaceutically acceptable salt of bendamustine, for example, bendamustine hydrochloride, and at least one polyhydric alcohol surfactant.

"Organic solvents" for use in the invention are those organic solvents with limited miscibility in water, i.e., having a solubility of less than 9 g/100 mL in water. Preferred organic solvents for use in the invention include $C_{5-10}$alkanes (pentane, hexane, heptane, octane, nonane, decane, and the like, as well as mixtures thereof), ethyl acetate, dichloromethane, diethyl ether, and the like, with $C_{5-10}$alkanes being particularly preferred. Hexane is an exemplary organic solvent for use in the invention.

Within the scope of the invention, polyhydric alcohol surfactants are included to help stabilize the emulsion. "Polyhydric alcohol surfactants" for use in the invention include a plurality of —OH moieties, at least some of which are capable are reacting with an isocyanate moiety to form a —O—C(O)—NH— group. Polyhydric alcohol surfactants are known in the art and include sorbitan esters, for example, polysorbate-based surfactants that are polyoxyethylene derivatives of sorbitan monolaurate. Examples of such polyhydric alcohol surfactants include Tween 20™ and Tween 80™. Other examples of sorbitan esters include surfactants derived from polyethoxylated sorbitan and oleic acid, such as Span 20™.

In those embodiments of the invention comprising a pharmaceutically acceptable salt form of a therapeutic agent, the emulsion may be treated with an amount of base or an amount of acid sufficient to convert the pharmaceutically acceptable salt form of the therapeutic agent into the free acid or free base form of the therapeutic agent. Suitable bases include amine based such as ammonia or an alkyl amine. Preferred alkyl amines include diethyl amine and N,N-dimethyl hexadecylamine. Preferred acids include hydrochloride acid, sulfuric acid, nitric acid, acetic acid, phosphoric acid, and the like.

In preferred embodiments of the invention, the emulsions of the invention are formed by mixing a continuous phase comprising an organic solvent, a dispersed phase comprising an aqueous solution of a pharmaceutically acceptable salt of bendamustine, and at least one polyhydric alcohol surfactant. The emulsion is then treated with an amount of base sufficient to convert the pharmaceutically acceptable salt of bendamustine to bendamustine free base. The base is preferably an amine base such as ammonia or an alkyl amine, with N,N-dimethyl hexadecylamine being particularly preferred. It is believed that by converting the salt form of bendamustine to bendamustine free base, which is much less soluble in water, a significant portion of the free base precipitates out of the aqueous solution, while still being retained in the dispersed "droplets," thereby minimizing the degree to which the bendamustine becomes degraded by contact with the aqueous solution.

According to the invention, the emulsions of the invention are treated with a compound comprising at least two isocyanate (—N=C=O) moieties. While compounds including a plurality of isocyanate moieties, for example, greater than 20 isocyanate moieties, are within the scope of the invention, preferred compounds for use in the invention have between two and ten isocyanate moieties. Exemplary embodiments of the invention include compounds having either two or four isocyanate moieties, with diisocyanate compounds (i.e., compounds having two isocyanate moieties) being particularly preferred. Compounds containing at least two isocyanate moieties are known and/or are commercially available. In most preferred embodiments of the invention, the compound comprising at least two isocyanate moieties is an alkyldiisocyanate, for example, 1,6-hexyl diisocyanate.

Treating the emulsion with the isocyanate-containing compound results in polymerization of the isocyanate groups with the at least one polyhydric alcohol surfactant. The polymerization occurs via the reaction of at least some of the —OH moieties of the at least one polyhydric alcohol surfactant with at least some of the isocyanate groups of the isocyanate-containing compound to form —O—C(O)—NH— linkages. Within the scope of the invention, polyhydric alcohol surfactant compounds are the only monomers in the emulsion available for polymerization with the isocyanate-containing. As such, the resulting polymers of the invention are formed only from the isocyanate-containing compound and the at least one polyhydric alcohol surfactant. These resulting polymers form the particles of the invention, which may or may not include therapeutic agents. Preferably, these resulting polymers form the polymeric shells of the nanocapsules of the invention.

The polymerization of the isocyanate-containing compound and the at least one polyhydric alcohol surfactant occurs at the water-polyhydric alcohol interface to form the particles of the invention. The polymerization can include cross-linking, that is, linking of one polymer chain to another. The degree of polymerization can be calculated using the Carother's equation, which is understood to those of skill in the art. See, e.g., Cowie J. M. G. "Polymers: Chemistry & Physics of Modern Materials (2nd edition, Blackie 1991), p. 29; Rudin Alfred "The Elements of Polymer Science and Engineering", Academic Press 1982, p. 171; Allcock Harry R., Lampe Frederick W. and Mark James E. "Contemporary Polymer Chemistry" (3rd ed., Pearson 2003) p. 324; Carothers, Wallace (1936). "Polymers and polyfunctionality". Transaction of the Faraday Society 32: 39-49.

The amount of isocyanate-containing compound necessary to sufficiently polymerize with the polyhydric alcohol surfactant to form the particles of the invention will varying depending on the amount of polyhydric alcohol surfactant used, as well as the chemical composition of the polyhydric alcohol surfactant used. Those skilled in the art will, however, be able to readily determine the amount of isocyanate-containing compound necessary to sufficiently polymerize with the polyhydric alcohol surfactant to form the particles of the invention using routine experimentation.

The amount of time compound necessary to sufficiently polymerize the isocyanate-containing compound with the polyhydric alcohol surfactant to form the particles of the invention will vary depending on, for example, the respective chemical compositions of the isocyanate-containing compound and the polyhydric alcohol surfactant. Those skilled in the art will, however, be able to determine the amount of time sufficient to form the particles of the invention using routine experimentation.

In some embodiments of the invention, the emulsion is treated with a compound comprising at least two isocyanate moieties for a time sufficient for the compound comprising at least two isocyanate moieties to polymerize with the at least one polyhydric alcohol surfactant at the aqueous phase-polyhydric alcohol interface to form the particles of the invention.

In preferred embodiments of the invention, the emulsion is treated with a compound comprising at least two isocyanate moieties for a time sufficient for the isocyanate-containing compound to polymerize with the at least one polyhydric alcohol surfactant at the water-polyhydric alcohol interface to form the bendamustine free base-containing particles of the invention. In particularly preferred embodiments, this process produces bendamustine free base-containing nanocapsules of the invention In some embodiments of the invention, the compound comprising at least two isocyanate moieties can further comprise at least one pH-sensitive moiety. It is envisioned that the pH-sensitive moiety will, when the particles of the invention are exposed to either higher or lower pH, cleave, hydrolyze, or otherwise change the chemical or physical properties of the particles of the invention. One exemplary pH-sensitive moiety is a tetrahydropyran moiety, which hydrolyzes at acidic pH. Other pH-sensitive moieties include esters, hydrazones, carboxy dimethylmaleic anhydrides, orthoesters, imines, β-thiopropionates, vinylethers, and phophoramidates. See, e.g., Gao, W. et al., pH-Responsive Nanoparticles for Drug Delivery, Molecular Pharmaceutics, vol. 7, no. 6, 1913-1920 (2010). One method for incorporating a pH-sensitive moiety into the compounds of the invention is set forth in the following scheme:

In some embodiments of the invention, the compound comprising at least two isocyanate moieties can also comprise at least one water-solubilizing moiety. "Water-solubilizing moieties" within the scope of the invention include hydrophilic groups. Hydrophilic groups are known in the art and include hydroxyl groups, carbonyl groups, carboxylic acid groups, amino groups, thiol groups, phosphate groups, ether groups, ester groups, phosphodiester groups, glycolytic groups, and peptide groups. Exemplary water-solubilizing moieties include those compounds having polyethylene glycol (PEG) moieties, functionalized PEG moieties, and mixtures thereof. In these embodiments of the invention, the resulting particles will include water-solubilizing moieties.

In some embodiments of the invention, the compound comprising at least two isocyanate moieties can also comprise at least one maleimide moiety. Maleimide moieties are activated alkenes that are excellent Michael acceptors. Maleimide moieties can be reacted with a variety of nucleophiles (Michael donors) so as to link the nucleophile to the maleimide moiety. Suitable nucleophiles can comprise pH-sensitive moieties such as those described herein.

Suitable nucleophiles for Michael addition with the maleimide moiety can also comprise at least one water-solubilizing moiety such as those described herein. Examples of nucleophiles comprising at least one water-solubilizing moiety, suitable for reaction with the maleimide moieties of the invention, include thiol-PEGs (SH-PEG-containing compounds) and amino-PEGs ($NH_2$-PEG-containing compounds).

In certain nanocapsule embodiments of the invention, the polymeric shell of the nanocapsules can optionally comprise at least one pH-sensitive moiety. It is envisioned that the pH-sensitive moiety will, when exposed to either higher or lower pH, cleave or hydrolyze. This cleavage or hydrolysis will result in the "opening" of the polymeric shell of the nanocapsules so as to allow for any therapeutic agents encapsulated within the nanocapsules to be released to the surrounding environment. One exemplary pH-sensitive moiety is a tetrahydropyran moiety, which hydrolyzes at acidic pH. Other pH-sensitive moieties include esters, hydrazones, carboxy dimethylmaleic anhydrides, orthoesters, imines, β-thiopropionates, vinylethers, and phophoramidates. See, e.g., Gao, W. et al., pH-Responsive Nanoparticles for Drug Delivery, Molecular Pharmaceutics, vol. 7, no. 6, 1913-1920 (2010).

In certain embodiments of the invention, the polymeric shell of the particles can optionally comprise at least one maleimide moiety. Within one embodiment over the invention, the particles comprising at least one maleimide moiety can be reacted with a nucleophile that comprises at least one water-solubilizing compound so as to link the water-solubilizing compound to the particle, using the maleimide moiety as a linker. Examples of nucleophiles comprising at least one water-solubilizing moiety, suitable for reaction with the maleimide moieties of the invention, include thiol-PEGs (SH-PEG-containing compounds) and amino-PEGs ($NH_2$-PEG-containing compounds). As such, some embodiments of the invention include particles wherein the polymeric shell comprises at least one PEG moiety.

In some embodiments of the invention, the polymeric shell of the particles optionally comprises at least one targeting ligand. As used herein, "targeting ligand" includes any compound, moiety, or residue having, or being capable of promoting, a targeting activity towards tissues and/or receptors in vivo. Targets with which a targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, immunoglobulins and cytoplasmic receptors for steroid hormones. Examples of suitable targeting ligands include, for instance, proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents including substituted small molecules and genetic material, including nucleosides, nucleotides and polynucleotides and mimetics thereof, such as peptide nucleic acids.

In some embodiments of the invention, the particles formed according to the described methods can be isolated. The particles can be isolated using any of the methods known in the art. Preferably, isolation of the particles includes optionally evaporating the organic solvent and dispersing the particles in an aqueous solution to form an aqueous dispersion of the particles. The particles can be further isolated by spray-drying the aqueous dispersion of the particles. Alternatively, the aqueous dispersion of the particles can be lyophilized using methods known in the art.

Also within the scope of the invention are pharmaceutical compositions comprising the particles of the invention and a pharmaceutically acceptable diluent or excipient. A "pharmaceutically acceptable carrier or diluent" includes any and all solvents, bulking agents, stabilizing agents, dispersion media, coatings, antibacterial and antifungal agents, isotonic and absorption delaying agents, and the like which are physiologically compatible. Examples of pharmaceutically acceptable carriers and diluents include one or more of water, saline, phosphate buffered saline, dextrose, glycerol, ethanol, and the like as well as combinations thereof. In many cases it will be preferable to include one or more isotonic agents, for example, sugars such as trehalose and sucrose, polyalcohols such as mannitol, sorbitol, or sodium chloride in the composition. Pharmaceutically acceptable substances such as wetting or minor amounts of auxiliary substances such as wetting or emulsifying agents, preservatives or buffers, are also within the scope of the invention.

Pharmaceutical compositions of the invention include nanocapsules of the invention, preferably bendamustine-containing nanocapsules, and a pharmaceutically acceptable diluent or excipient. One exemplary pharmaceutically acceptable diluent is phosphate-buffered saline (PBS).

The particles of the invention can be used, either alone or as part of a pharmaceutical composition, to treat cancer in a patient. These methods comprise administering the particles of the invention, either alone or as part of a pharmaceutical composition, to a patient in need of treatment. Preferred cancers that can be treated using the methods of the invention include solid or non-solid tumors such as, for example, chronic lymphocytic leukemia, Hodgkin's disease, indolent non-Hodgkin's lymphoma (T-cell lymphoma, B-cell lymphoma), aggressive non-Hodgkin's lymphoma, multiple myeloma, acute lymphocytic leukemia, breast cancer or lung cancer. Other solid and non-solid cancer tumors are also envisioned as being treatable with compounds and compositions of the invention, such as for example, sarcoma, bladder cancer, cervical cancer, testicular cancer, melanoma, glioblastoma, colon cancer, head and neck cancer, ovarian cancer, and prostate cancer. Additional solid and non-solid cancer tumors are also envisioned as being treatable with compounds of the invention, for example, breast cancer.

In one embodiment of the invention, the compounds and compositions of the invention are used to treat patients who are resistant to one or more chemotherapeutic agents, such as, for example, alkylating agents. Exemplary alkylating agents to which patients may be resistant include: nitrogen mustards; ethylenimes; alkylsulfonates; triazenes; piperazines; and nitrosureas. More specific examples of the various types of chemotherapeutic agents to which patients can become resistant are listed below. Patients resistant to one or more of these agents would benefit by treatment with the compounds and compositions of the invention.

Nitrogen Mustards

Mechlorethamine, marketed under the trade name Mustargen®, is given by injection to treat Hodgkin's disease and non-Hodgkin's lymphoma, and as a palliative therapy for breast and lung cancers, and given as a topical treatment for skin lesions of mycosis fungoides (cutaneous T-cell lymphoma).

Ifosfamide, sold under the trade name Ifex®, is used to treat both Hodgkin's and non-Hodgkin's lymphoma, as well as recurrent testicular cancer and germ cell tumors, sarcomas, lung cancer, bladder cancer, head and neck cancer, and cervical cancer.

Melphalan is a chemotherapy drug sold under the brand name Alkeran®, and is also referred to as L-PAM or phenylalanine mustard. It is used to treat multiple myeloma, ovarian cancer, neuroblastoma, rhabdomyosarcoma, and breast cancer.

Chlorambucil is sold by the trade name Leukeran®, and is most widely used to treat chronic lymphocytic leukemia, malignant lymphomas including lymphosarcoma, giant follicular lymphoma, and Hodgkin's disease. It has also been successfully used to treat non-Hodgkin's lymphoma, breast, ovarian and testicular cancer, Waldenstrom's macroglobulinemia, thrombocythemia, and choriocarcinoma.

Cyclophosphamide is marketed as Cytoxan® or Neosar®, and is used to treat Hodgkin's and non-Hodgkin's lymphoma, Burkitt's lymphoma, chronic lymphocytic leukemia, chronic myelocytic leukemia, acute myelocytic leukemia, acute lymphocytic leukemia, t-cell lymphoma, multiple myeloma, neuroblastoma, retinoblastoma, rhabdomyosarcoma, Ewing's sarcoma; breast, testicular, endometrial, ovarian, and lung cancers.

Nitrosoureas

Streptozocin is sold under the trade name Zanosar®, and is used to treat islet cell pancreatic cancer.

Carmustine is also known as BiCNU® or BCNU, and is used for some kinds of brain tumors, glioblastoma, brainstem glioma, medulloblastoma, astrocytoma, ependymoma, and metastatic brain tumors. It is also used in treatment for multiple myeloma, Hodgkin's disease, non-Hodgkin's lymphoma, melanoma, lung cancer, and colon cancer.

Lomustine, also known as CCNU or CeeNU®, is used to treat primary and metastatic brain tumors, Hodgkin's disease and non-Hodgkin's lymphoma, and has also been used for melanoma, lung, and colon cancer.

Alkyl Sulfonates

Busulfan, sold under trade names Busulfex® and Myleran®, is used to treat chronic myelogenous leukemia.

Triazines

Dacarbazine is sold under the trade name DTIC-Dome® and is used to treat metastatic malignant melanoma, Hodgkin's disease, soft tissue sarcomas, neuroblastoma, fibrosarcomas, rhabdomyosarcoma, islet cell carcinoma, and medullary thyroid carcinoma.

Temozolomide is sold under the trade name Temodar®, and is used to treat the specific types of brain tumors anaplastic astrocytoma and glioblastoma multiforme.

Ethylenimines

Thiotepa, known under the trade name Thioplex®, is an alkylating agent used to treat breast cancer, ovarian cancer, Hodgkin's disease, and non-Hodgkin's lymphoma.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$alkyl" refers to an alkyl radical containing from 1 to 4 carbon atoms.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention. In some embodiments, the pharmaceutical compositions can be prepared in accordance with acceptable pharmaceutical procedures, such as described in Remington's Pharmaceutical Sciences, 17th edition, ed. Alfonoso R. Gennaro, Mack Publishing Company, Easton, Pa. (1985).

As used herein, "solid tumor" refers to a malignant tumor that is a localized mass of tissue. Examples of solid cancer tumors include lymphomas, sarcomas, and carcinomas and include breast cancer, brain cancer, bone cancer, colon cancer, pancreatic cancer, lung cancer, and the like.

As used herein, a "non-solid tumor cancer" refers most commonly to hematologic cancers, that is, malignant cancers of the blood. Examples of non-solid tumor cancers include chronic lymphocytic leukemia, Hodgkin's disease, indolent non-Hodgkin's lymphoma (T-cell lymphoma, B-cell lymphoma), multiple myeloma, and the like.

General Procedure for Preparing Particles of the Invention

The nanocapsules were formed using a W/O nanoemulsion process, which takes bendamustine hydrochloride dissolved in a water phase (W) and emulsifies it with an oil phase (O) containing a polyhydric alcohol surfactant system. The resulting W/O emulsion was then treated with a base ($NH_3$ or alkyl amine) which precipitated the bendamustine hydrochloride salt as the free base, increasing the compound's stability to hydrolysis in the aqueous environment. The precipitation process was shown not to destabilize the particle size of the resulting water droplets. The system was then treated with a diisocyante compound that reacts with the polyhydric alcohol surfactants (Span and Tween) which react as a cross-linking agent for the diisocyante groups. The resulting condensation polymerization occurred primarily at the water-oil interface when the isocyanate moiety contacted the surfactant head groups. The encapsulation of the bendamustine free base was shown to be complete with as little as 25 uL of 1,6-hexyl diisocyante.

The solvent (hexanes) was then be removed by heating, rotary-evaporation or spray drying to obtain the polymeric shell particles of the invention as nanocapsules. The nanocapsules were converted to an aqueous system by dispersion in water using an appropriate surfactant system (HSA, PVA etc). The shells of the nanocapsules comprised mixtures of carbamates and ureas which resisted dissolution is pure organic solvents. The lyophilized nanoparticles were reconstituted and analyzed using cryo-Transmission Electron Microscopy (c-TEM). The majority of the nanoparticles were 20-40 nm solid spheres that were readily dispersed in water. A minority of particles were in the 125 nm range. The particles all had a smooth surface.

Bendamustine Nanocapsules: An oil phase was prepared by mixing 10 mL of Span 20 and 10 mL of Tween 80 in 113 mL of hexane. The oil phase was then added to an aqueous phase comprising 20 mL of a 25 mg/mL bendamustine HCl salt. This mixture was processed using an IKA Ultra-Turrex hand held homogenizer to obtain a nanoemulsion with particle size of 59.7 nm. The nanoemulsion was then stirred using a magnetic stir bar and treated with 500 µL N,N-Dimethylhexadecylamine to convert the bendamustine HCl salt to the bendamustine free base, which precipitates in the aqueous compartment of the nanocapsule. After ~5 minutes, 500 µL of 1,6-Hexyldiisocyanate was added and this mixture was stirred for 60 minutes to allow for formation of the polymer. The hexane suspension of nanocapsules was mixed with 300 mL of water (SWFI) and emulsified using a sonic probe homogenizer. The hexane and a portion of the water was removed from the resulting aqueous suspension using a rotory-evaporator to bring the volume to ~150 mL. The 150 mL was then mixed with 12 g of PVP C-17 and 30 g of mannitol as bulking agents and the total volume adjusted to 200 mL. This suspension was then portioned in 10 mL aliquots into 30 mL serum vials and lyophilized.

Cross-linking Experiment. Three nano-emulsions of bendamustine at 25 mg/mL in 0.5% PVA (2 mL) were prepared. Nano-emulsions were then treated with 5 μL, 15 μL, or 25 μL of hexyl diisocyanate. The mixtures were analyzed, using HPLC, before, immediately after addition, and 12 hours post-addition. Samples taken before hexyl diisocyanate addition showed expected levels of bendamustine via HPLC. The samples taken at 12 hours post-addition showed that between 15 and 25 μL of monomer (hexyl diisocyanate) is required for encapsulation of bendamustine within the nanocapsules of the invention.

EM Grid Preparation

Sample was solubilized by adding 2.0 mL of ddH2O to 5 mg of sample and vortexing for one minute. The sample was preserved in vitrified ice supported by carbon coated holey carbon films on 400 mesh copper grids. The sample was prepared by applying a 3 μL drop of undiluted sample solution to a cleaned grid, blotting away with filter paper and immediately proceeding with vitrification in liquid ethane. Grids were stored under liquid nitrogen until transferred to the electron microscope for imaging.

EM Imaging

Electron microscopy was performed using an FEI Tecnai T12 electron microscope, operating at 120 KeV equipped with an FEI Eagle 4K×4K CCD camera. The grid was transferred into the electron microscope using a cryostage that maintains grids at a temperature below −170 C. Images of the grid were acquired at multiple scales to assess the overall distribution of the specimen. After identifying potentially suitable target areas for imaging at lower magnifications, high magnification images were acquired at nominal magnifications of 110,000× (0.10 nm/pixel), 67,000× (0.16 nm/pixel), 52,000× (0.21 nm/pixel), and 21,000× (0.50 nm/pixel). The images were acquired at a nominal underfocus of −2.5 to −1.5 μM (110,000×), −3 μM (67,000×), −4 μM (52,000×) and −5 μM (21,000×) and electron doses of ~10-15 e/Å2.

Cryo transmission electron microscopy of certain nanocapsules of the invention demonstrated that the outer layer of the nanocapsules is consistent with the appearance of a lipid bilayer both in appearance and thickness (about 6-8 nm). The diameter of the nanocapsules ranged from about 20 nm to about 600 nm. Filled nanocapsules contain what appeared to be smaller nanoparticles.

Figure 1:
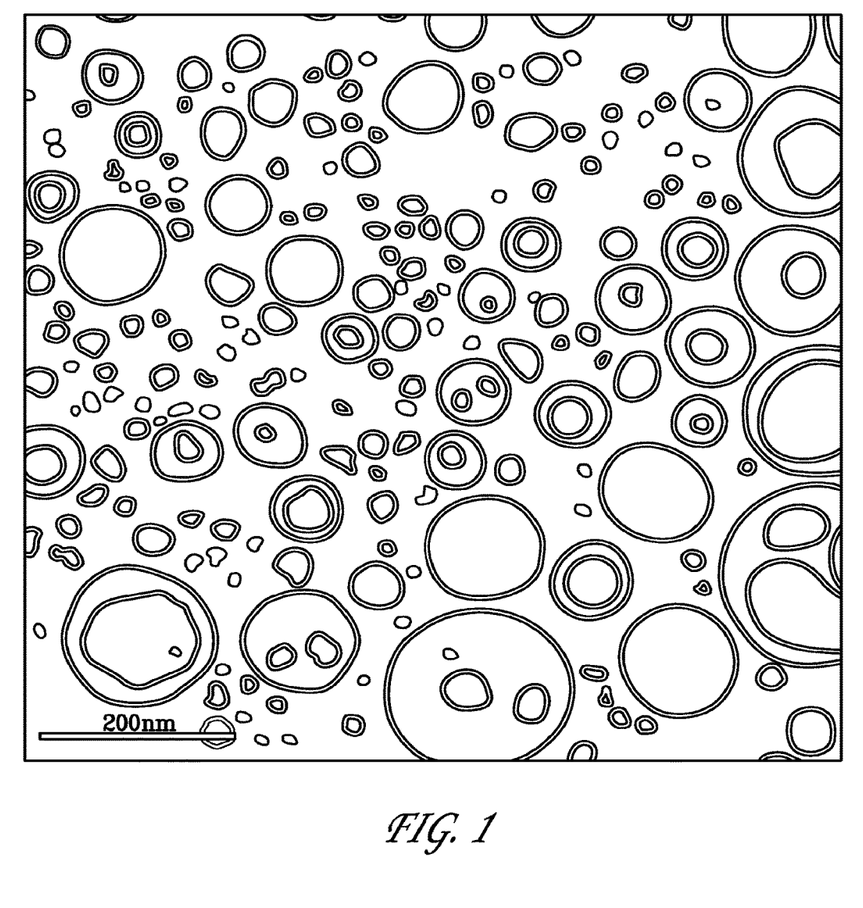
FIG. 1 depicts an electron microscopy image of one embodiment of bendamustine free base-containing particles of the invention.

FIG. 1 depicts an image of a sample of bendamustine free base-containing nanocapsules of the invention, preserved in vitreous ice at a magnification of 52,000×. The inser shows a small area of the image at a larger scale.

Figure 2:
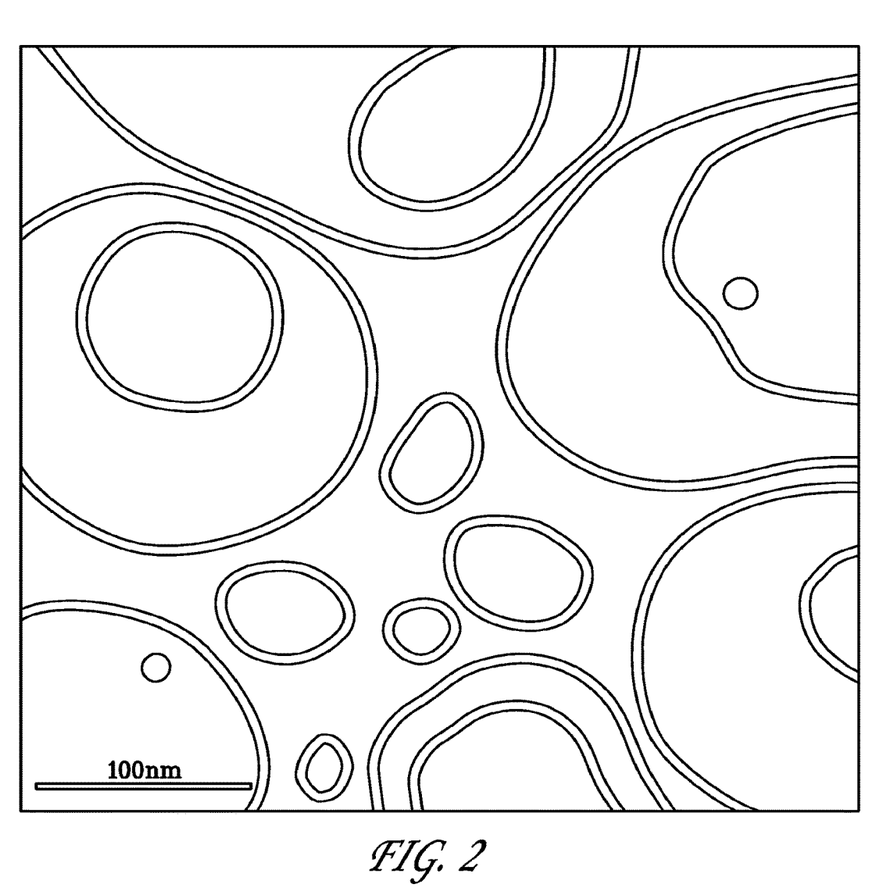
FIG. 2 depicts an electron microscopy image of one embodiment of bendamustine free base-containing particles of the invention.

FIG. 2 depicts an image of a sample of bendamustine free base-containing nanocapsules of the invention, preserved in vitreous ice at a magnification of 110,000×.

What is claimed:

1. Particles comprising
    a core comprising a therapeutic agent; and
    a shell surrounding the core and comprising a polymer polymerized from
        a compound comprising at least two isocyanate moieties; and
        at least one polyhydric alcohol surfactant that is derived from a polyethoxylated sorbitan and oleic acid, a polyoxyethylene derivative of sorbitan monolaurate, a sorbitan ester, or a mixture thereof,
    wherein the particles have an average diameter of between about 20 nm to about 800 nm.

2. The particles of claim 1, wherein the therapeutic agent is water soluble.

3. The particles of claim 1, wherein the therapeutic agent is a peptide or protein.

4. The particles of claim 1, wherein the therapeutic agent is a polynucleotide.

5. The particles of claim 1, wherein the therapeutic agent is a small molecule drug compound.

6. The particles of claim 1, wherein the particles have an average diameter of between about 50 nm and about 300 nm, about 60 nm to about 600 nm, or about 20 nm to about 600 nm.

7. The particles of claim 1, wherein the compound comprising at least two isocyanate moieties further comprises at least one pH-sensitive moiety.

8. The particles of claim 1, wherein the compound comprising at least two isocyanate moieties further comprises at least one maleimide moiety.

9. The particles of claim 8, wherein the at least one maleimide moiety serves as a linker to connect at least one pH-sensitive moiety to the compound.

10. The particles of claim 7, wherein the pH-sensitive moiety is a tetrahydropyran moiety.

11. The particles of claim 1, wherein the compound comprising at least two isocyanate moieties further comprises at least one water-solubilizing moiety.

12. The particles of claim 11, wherein the at least one maleimide moiety serves as a linker to connect at least one water-solubilizing moiety to the compound.

13. The particles of claim 11, wherein the at least one water-solubilizing moiety is a PEG moiety, a functionalized PEG moiety, or a mixture thereof.

14. The particles of claim 1, wherein the compound comprising at least two isocyanate moieties has between four and ten isocyanate moieties.

15. The particles of claim 1, wherein the compound comprising at least two isocyanate moieties is a diisocyanate.

16. The particles of claim 15, wherein the compound comprising at least two isocyanate moieties is an alkyldiisocyanate.

17. The particles of claim 16, wherein the compound comprising at least two isocyanate moieties is 1,6-hexyl diisocyanate.

18. The particles of claim 1, wherein the particles are nanoparticles.

19. The particles of claim 1, wherein the particles are nanocapsules.

20. The particles of claim 1, wherein the polymeric shell comprises at least one targeting ligand.

21. A pharmaceutical composition comprising the particles of claim 1 and a pharmaceutically acceptable diluent or excipient.

22. A method of treatment comprising administering to a patient in need thereof, the pharmaceutical composition of claim 21.

* * * * *